United States Patent [19]

Sramek

[11] 4,343,314

[45] Aug. 10, 1982

[54] NON-INVASIVE REAL TIME BLOOD PRESSURE MEASUREMENT SYSTEM

[76] Inventor: Bohumir Sramek, 19211 Edgehill Dr., Irvine, Calif. 92715

[21] Appl. No.: 177,061

[22] Filed: Aug. 11, 1980

[51] Int. Cl.³ .............................................. A61B 5/02
[52] U.S. Cl. .................................. 128/680; 128/681; 128/682; 128/683
[58] Field of Search ............................... 128/677–683, 128/687–690, 694

[56] References Cited

U.S. PATENT DOCUMENTS 3,552,381  1/1971  Burns et al. ......................... 128/681

OTHER PUBLICATIONS

Darling, R. C. et al., "Quantitative Segmental Pulse Volume Recorder: A Clinical Tool", *Surgery,* vol. 72, #6, Dec. 1972, pp. 873–887.

*Primary Examiner*—Robert W. Michell
*Assistant Examiner*—Francis J. Jaworski
*Attorney, Agent, or Firm*—Knobbe, Martens, Olson, Hubbard & Bear

[57] ABSTRACT

A non-invasive, real time blood pressure measurement system includes a cuff connected to a pump, a cuff pressure sensor, and a detector to sense the times when the cuff stops or starts blood flow in a user's body appendage. The pump cyclically varies the cuff pressure from above systolic to below diastolic levels at a relatively fast rate compared to the heartbeat rate enabling blood pressure measurements to be made quickly in sequence. Electrical circuitry is provided to make the blood pressure measurement by correlating the cuff pressure with the detected times. This system is compatible with major types of automatic sphygmomanometric systems.

17 Claims, 4 Drawing Figures

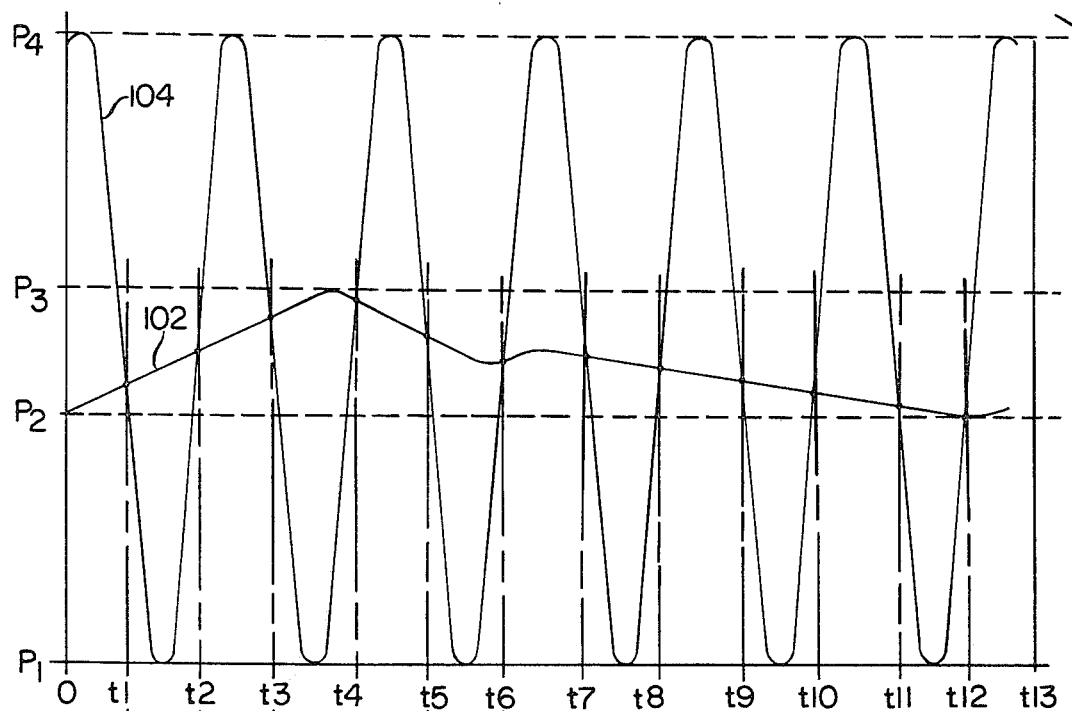
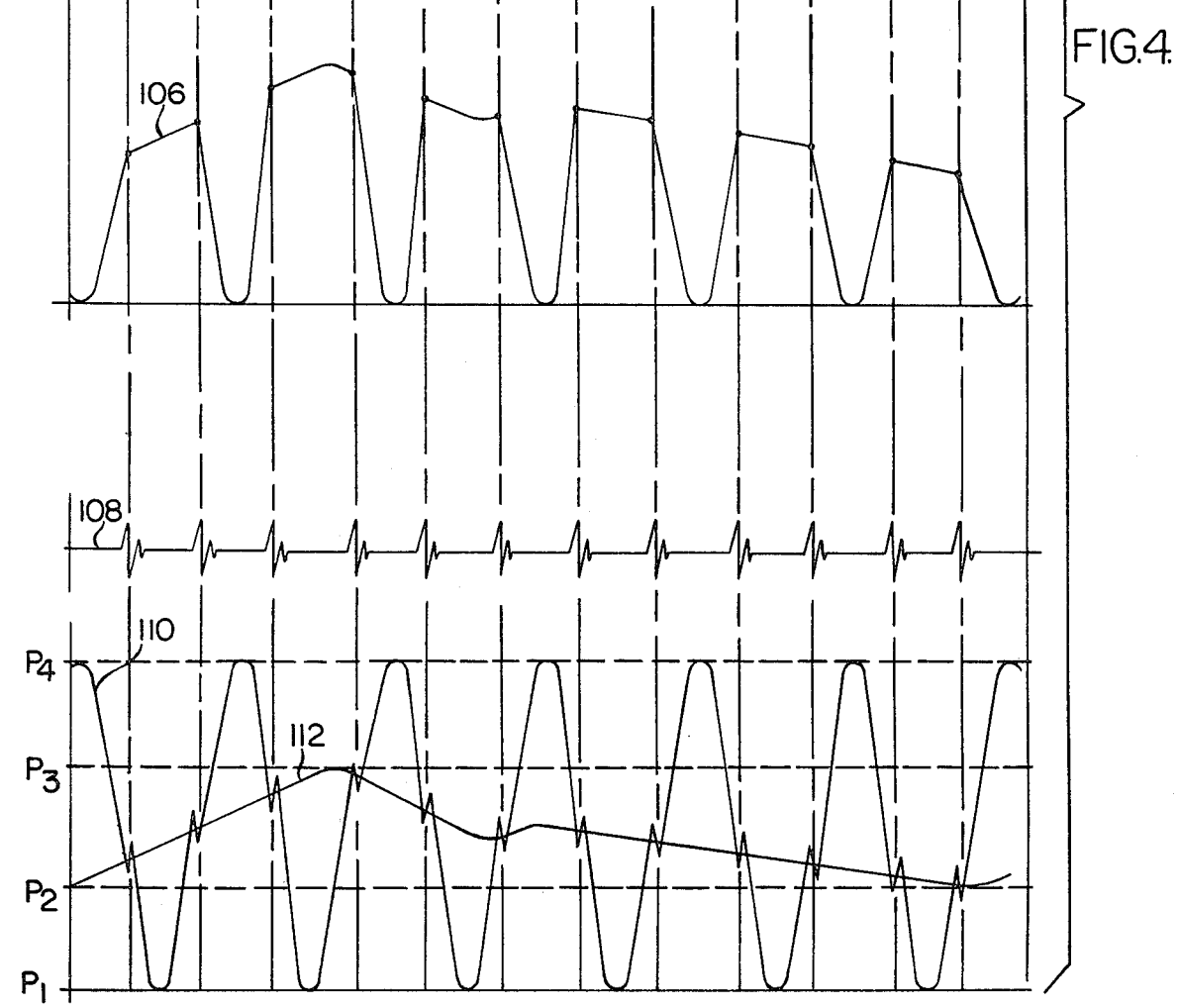
FIG.4.

NON-INVASIVE REAL TIME BLOOD PRESSURE MEASUREMENT SYSTEM

BACKGROUND OF THE INVENTION

This invention relates generally to medical devices for measuring blood pressure and pertains more particularly to cuff-type systems employing a pump and transducers.

Many types of blood pressure measurement devices are known in the prior art. One example is U.S. Pat. No. 4,105,021 to Williams et al which shows a system for applying an occluding inflatable cuff to a body member, with the pressure applied thereby being cycled between a pressure greater than systolic and a pressure less than diastolic. The pressurization cycle described in this patent occurs as a controlled bleed of pressure from the occluding cuff during the time that a plurality of blood pressure pulses occur. The patent shows the use of a blood flow monitor and a pressure monitor to measure pressure inside the cuff. A similar system is described by Fletcher et al in U.S. Pat. No. 3,814,083, which describes a bleed-down of the cuff pressure which was from 160-60 mm Hg in 30 seconds. Both patents contemplate measuring both systolic and diastolic blood pressure during a single cycle of the occluding cuff pressure.

Blood pressure measurement systems are also described by Lichowsky in U.S. Pat. No. 3,905,354 which shows the measurement of pressure fluctuations in a chamber attached to a patient's arm, wherein the fluctuations correspond to heartbeats of the patient. Similarly, U.S. Pat. No. 4,074,711 to Link et al discloses a transducer for measuring the fluctuating component of a cuff pressure, which is representative of the pulsatile blood pressure.

A major problem with prior art methods of measuring blood pressure non-invasively is that the process of obtaining a measurement requires an undesirably long period of time. A problem faced with such prior art devices is that the user is unable to tell what the blood pressure is instantaneously and to tell how the blood pressure has changed over the period of a few heartbeats. A further problem faced by such prior art devices is that the accuracy of blood pressure measurements during a cuff pressure cycle may be degraded if the blood pressure is not steady.

SUMMARY OF THE INVENTION

Accordingly, it is an object of this invention to provide a blood pressure measurement system.

This invention involves a blood pressure measurement system which includes a pump and, attached to the pump, a cuff for encircling a body appendage of a user. The pump provides an oscillating pressure to the cuff at a frequency higher than the blood pressure frequency. The cuff pressure is monitored and a detector is used to detect when the cuff pressure is equal to the blood pressure. The detector may be any one of various types used to sense blood flow, Korotkoff sounds, or discontinuities in the cuff pressure. An electrical circuit is provided, either in analog or digital form, to correlate the cuff pressure with the detected times and thus to determine instantaneous values of blood pressure at the detected times. A display may be provided to show a waveform envelope of the sequential blood pressure measurements.

A significant feature of this invention is that it provides a non-invasive blood pressure measurement system which performs blood pressure measurements on a real time basis, i.e., the measurements substantially reflect the instantaneous blood pressure.

Another advantage of the invention is that highly accurate blood pressure measurements are achieved with a non-invasive device.

A further feature of the invention is that it provides a blood pressure measurement system which generates a sequence of substantially continuous blood pressure measurements.

Another feature of the invention is that it is compatible with major types of automated sphygmomanometric systems.

These and other advantages of this invention will appear more fully from the following description made in conjunction with the accompanying drawings wherein like reference characters refer to the same or similar parts throughout the several views.

DESCRIPTION OF THE DRAWINGS

FIG. 4 is a waveform diagram depicting the amplitude versus time behavior of various quantities relevant to this invention.

DESCRIPTION OF THE PREFERRED EMBODIMENT

Figure 1:
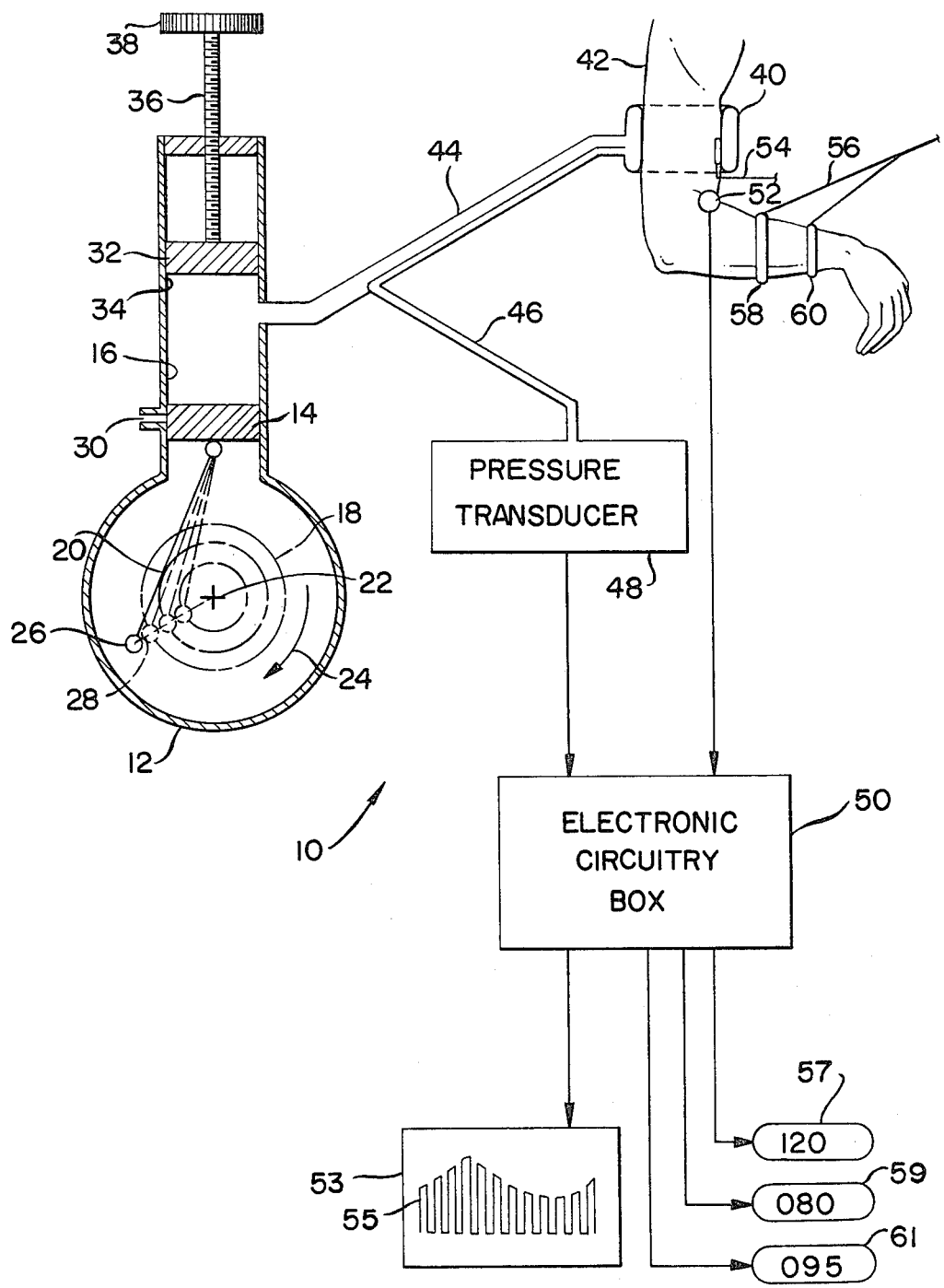
FIG. 1 is a pictorial diagram of the blood pressure measurement system of this invention showing electronic elements in block diagram form.

Referring first to FIG. 1, blood pressure measurement system 10 includes a pump 12 having a piston 14 slidably mounted to cyclically reciprocate in pump cylinder 16. Piston 14 is connected to crankshaft 18 by means of crank 20, so that piston 14 reciprocates cyclically as shaft 18 is rotated about shaft axis 22 in the direction of arrow 24. The stroke of piston 14 is adjustable by moving end 26 of crank 20 along the radius 28 of shaft 22. Shaft 22 is rotated by an external power source (not shown) such as an electric motor.

Port 30 is a hole extending through the wall of cylinder 16 and is positioned along the length of cylinder 16 so that port 30 is at the lowermost portion of the strike of piston 14. Thus, port 30 is located so as to allow pump cylinder 16 to vent through port 30 when piston 14 reciprocates to the lowest point of its strike during each cycle. Port 30 insures that the inside of cylinder 16 is equalized to atmospheric pressure at least once during each cycle of piston 14. Note that port 30 is either covered by or behind piston 14 when piston 14 is not in its lowermost stroke position.

Volume control piston 32 is slidably mounted inside volume control cylinder 34, which is coaxial and continuous with cylinder 16. Adjustment screw 36 is threadably mounted through cylinder 16 and has a knob 38 mounted on the outside end thereof. Screw 36 is connected to piston 32 so that turning screw 36 moves piston 32 along the length of cylinder 34. Thus, the location of piston 32 may be changed to vary the volume inside cylinder 34.

Inflatable occlusion cuff 40 is preferably composed of a flexible material for encircling a body appendage 42 (for example, an arm) of the user. Cuff 40 is of the usual construction adapted for occluding blood vessels in appendage 42 when pressure is supplied to cuff 40.

Pressure supply tube 44 provides a fluidic connection between cuff 40 and the insides of pump cylinder 16 and volume control cylinder 34 so that all are fluidicly connected and filled with a fluid. Note that when piston 14 blocks the vent 30, a substantially closed volume is formed by cuff 40, tube 44, cylinder 34 and cylinder 16. This fluid may be a gas such as air or a liquid such as a low viscosity oil. The volume of such fluid required varies with its compressability. For a fluid such as air, a volume of between 250 and 300 cubic centimeters is suitable. For a fluid such as a low viscosity oil, a volume of between 10 and 20 cubic centimeters is suitable. When a fluid, such as low viscosity oil, having a relatively low compressibility is used in this invention, it is preferable that cuff 40 be of the known, prior art type which is not substantially expansible in outside circumference.

Pressure measurement tube 46 is threaded along the inside of tube 44 and has an open distal end near cuff 40 and the opposite proximal end connected to pressure transducer 48. Tube 46 is placed inside tube 44 to minimize the number of connections which must be coupled to appendage 42, to thereby minimize the inconvenience to the user of having tubes or cables hanging from appendage 42. As described below, tube 46 and pressure transducer 48 are used to measure the fluid pressure inside cuff 40. Accordingly, the distal end of tube 46 is located near cuff 40 to avoid inaccuracies due to pressure drops along the length of tube 44.

Pressure transducer 48 may be any of the usual types of transducers (such as a diaphragm with a strain gauge) for converting fluid pressure to an electrical signal. Transducer 48 serves to measure the fluid pressure inside cuff 40 through tube 46. Transducer 48 is electrically connected to electronic circuitry box 50 to transfer an electrical signal indicative of the measured cuff fluid pressure.

Blood flow detector 52 is positioned on appendage 42 to detect the starting and stopping of blood flow in appendage 42 due to occlusion by cuff 40. Thus detector 52 detects the times at which the fluid pressure inside cuff 40 is equal to the blood pressure inside appendage 42. Detector 52 may be of the photoplethysmographic type known in the prior art including a photoelectric blood pulsation sensor positioned adjacent cuff 40. Such a sensor can also be used to sense blood volume pulsations (the pulse) which as described below is periodically interrupted by the pressures provided by cuff 40. Detector 52 is electrically connected to box 50 to transfer an electrical signal indicative of the blood flow in appendage 42.

In an alternative embodiment of this invention, microphone 54 is used as an alternative blood flow detector to detector 52. As shown in FIG. 1, microphone 54 mounts under cuff 40 on appendage 42 to detect Korotkoff sounds characteristic of turbulent blood flow resulting from occluding blood vessels, as is known in the prior art. Microphone 54 thus detects the times at which the fluid pressure inside cuff 40 is equal to the blood pressure inside appendage 42. Microphone 54, if substituted for detector 52 in an embodiment of this invention, would be electrically connected to box 50 to transfer an electrical signal indicative of the blood flow in appendage 42.

Electrical impedance plethysmograph 56 also shown in FIG. 1 is a further alternative blood flow detector to detector 52 and is used as a part of an alternative embodiment of this invention. Impedance plethysmograph 56 includes a spaced-apart pair of electrical conductors 58 and 60 encircling the appendage 42, as is known in the prior art. The electrical impedance between conductors 58 and 60 is known to vary as a function of the blood flow, thus plethysmograph 56 also detects the times at which the fluid pressure inside cuff 40 is equal to the blood pressure inside appendage 42. Impedance plethysmograph 56, if substituted for detector 52 in an embodiment of this invention, would be electrically connected to box 50 to transfer an electrical signal indicative of the blood flow in appendage 42.

As described in detail below, electrical circuit box 50 correlates the cuff pressure measured by transducer 48 with the blood flow measurements of detector 52. The measurements made by detector 52 are used by box 50 to determine the times at which the fluid pressure inside cuff 40 is equal to the blood pressure in appendage 42. Box 50 correlates the times obtained by detector 52 with pressure measured by transducer 48 to generate an electrical blood pressure signal indicative of the blood pressure inside appendage 42.

Display 53 is preferably a video display electrically connected to box 50 for displaying a waveform 55 generated by box 50 indicative of the measured blood pressure. Waveform 55 preferably consists of a sequence of spaced-apart, parallel spikes; with the height of each of the spikes indicating an instantaneous blood pressure value; and with the separation of the spikes indicating time duration. Contrary to the impression which may be conveyed by the waveform 55 of FIG. 1 which has been drawn in a stylized fashion to accentuate the waveform 55, the spikes may be of quite narrow width (short time duration) compared to the width (time) separating the spikes. Also, the shapes of the tops of the spikes is not crucial to operation of the embodiment of the invention described herein. Of course, the exact characteristics of these spikes necessarily depends upon and varies with the monitoring equipment used; however, monitoring equipment may be used to produce an envelope of waveform 55 which resembles the envelope of the waveform of the blood pressure in appendage 42.

Displays 57, 59 and 61 are preferably digital character displays electrically connected to box 50 for displaying numerical digits indicative of the measured systolic, diastolic, and mean blood pressure, respectively. The contents of displays 57, 59 and 61 are generated by box 50 as a result of correlating the measurements of transducer 48 and detector 52 to determine the measured blood pressure and to generate the contents of displays 57, 59 and 61 based on the maximum, minimum, and mean, respectively, of the measured blood pressure.

Figure 2:
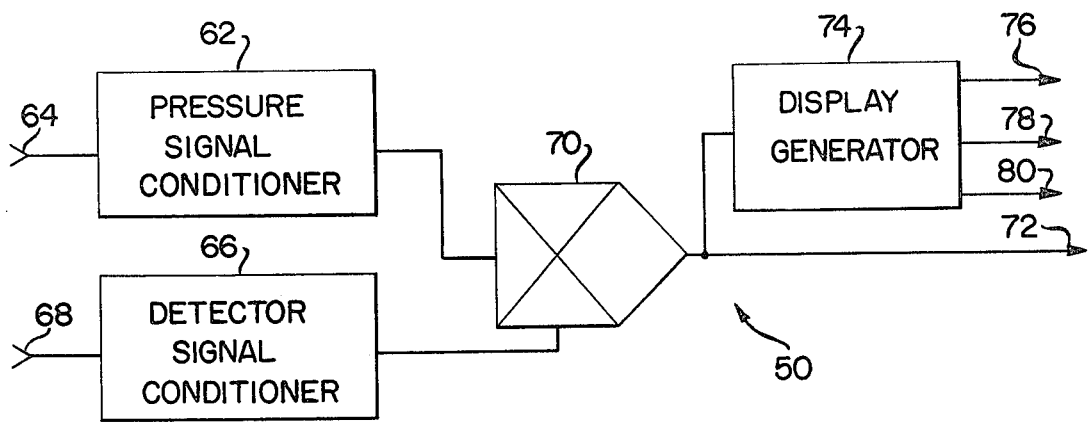
FIG. 2 is a block diagram of the analog electronic circuitry for use in an embodiment of this invention.

An analog electronic circuit implementation for the electronic box 50 is shown in FIG. 2. Pressure signal conditioner 62 has an input 64 for electrical connection to transducer 48 of FIG. 1. Conditioner 62 preferably comprises a power source for transducer 48 and an amplifier. Detector signal conditioner 66 has an input 68 for electrical connection to detector 52 of FIG. 1. Conditioner 66 preferably comprises a differentiator and a signal level triggering switch.

The output of conditioner 62 is provided as an input to gate 70 which is gated by the output of conditioner 66. Conditioner 66 gates the gate 70 when detector 52 (see FIG. 1) indicates that the pressure inside cuff 40 is the same as the blood pressure inside appendage 42, and allows the output of conditioner 62 to propagate through gate 70. The magnitude of the output of conditioner 62 is related to the pressure inside cuff 40. Thus output 72 of gate 70 has a waveform consisting of a sequence of spaced-apart spike pulses with a pulse corresponding to each time conditioner 66 gates the gate 70, and with the height of each pulse corresponding to the output of conditioner 62. Output 72 may be electrically connected to display 52 of FIG. 1.

Display generator 74 preferably comprises analog and digital electronic circuitry of the usual type for electrical connection to output 72 for generating outputs 76, 78 and 80 to drive the numeric displays 57, 59 and 61, respectively, of FIG. 1. For example, generator 74 may comprise prior art triggerable digital voltmeter circuits.

Pressure signal conditioner 62 may also include compensation circuitry, such as an analog delay line, to compensate for a time delay between detector 52 and transducer 48 due to detector 52 being positioned a distance away from cuff 40.

Figure 3:
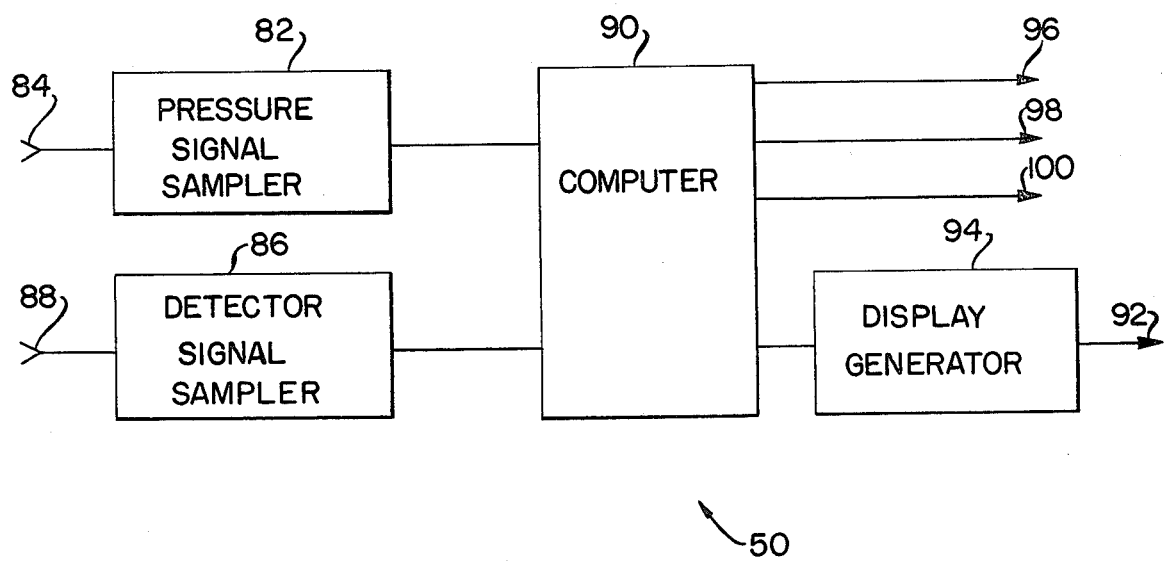
FIG. 3 is a block diagram of the digital electronic circuitry for use in an embodiment of this invention.

Referring next to FIG. 3, a digital electronic circuit implementation is shown for the electronic circuitry box 50 of FIG. 1. Pressure signal sampler 82 has an input 84 for electrical connection to transducer 48 of FIG. 1. Sampler 82 preferably comprises an analog to digital converter for sampling the results of pressure measurements made by transducer 48. Detector signal sampler 86 has an input 88 for electrical connection to detector 52 of FIG. 1. Sampler 86 preferably comprises an analog to digital converter for sampling the results of the blood flow measurements made by detector 52.

The outputs of samplers 82 and 86 are provided as an input to computer 90. Computer 90 correlates the outputs of samplers 82 and 86 by processing the digital data acquired from both so that data acquired from sampler 82 is selected which corresponds to data from sampler 86 indicating that the pressure inside cuff 40 is equal to the blood pressure in appendage 42. Essentially, computer 90 tests the data from sampler 86 to determine the times at which detector 52 indicated that blood flow had started or stopped, and then computer 90 selects data from sampler 82 corresponding to the times determined. The data selected by computer 90 is a digital electronic signal, composed of a plurality of binary bits inside computer 90, indicative of the blood pressure in appendage 42.

Outputs 96, 98 and 100 are digital output ports of computer 90 for driving displays 57, 59 and 61 respectively. Computer 90 performs internal mathematical calculations in a conventional, known manner with the data which it acquires from samplers 82 and 86 in order to generate the contents of displays 57, 59 and 61

A video output 92 is provided from display generator 94 to provide video signals to display 53 to produce waveform 55 or other waveforms representative of the measured blood pressure inside appendage 42. Display generator 94 is of the usual, conventional type of computer graphics system for connection to computer 90. Generator 94 operates to display the data processed by computer 90.

The operation of the invention is best explained using the waveforms 102 through 112 plotted in FIG. 4 on a common, horizontal time axis extending from 0 to 13. Waveform 102 represents the arterial blood pressure as it actually exists inside appendage 42 during a single heart beat. Waveform 104 represents the fluid pressure inside cuff 40 as measured by transducer 48. The vertical axis for the plot of waveforms 102 and 104 extends from pressure P1 through pressure P4.

Pressure P2 is the diastolic blood pressure and pressure P3 is the systolic blood pressure. Pump 12 periodically varies the pressure in the cuff 40 to produce the periodic waveform 104 which extends from P1 to P4 and passes through both the systolic and diastolic blood pressure levels. It is preferable that pressure P1 be equal to the atmospheric pressure so as to minimize the amount of time that venous blood flow in appendage 42 is occluded by cuff 40. Port 30 in pump cylinder 16 insures that pressure P1 will remain constant at the atmospheric pressure. The venting of cylinder 16 by port 30 occurs at the times indicated by pressure waveform 104 decreasing to pressure P1.

The period of blood pressure waveform 102 extends from 0 to t13. As illustrated, approximately six periods of cuff pressure waveform 140 occur during the period of waveform 102. The period and frequency of the blood pressure waveforms of human beings vary from person to person and are dependent on many factors such as physical condition and exertion. It is expected that the blood pressure waveform frequency (heart beat rate) may range from 50 to 150 beats per minute. It is preferable that the frequency of cuff pressure waveform 104 be relatively higher, on the order of 10 compressions per second. Thus, the period of waveform 104 is preferably substantially shorter than the period of waveform 102. Waveform 104 crosses over and intersects waveform 102 at the times indicated as t1 through t12. At those crossover points occurring at times t1 through t12, the pressure in cuff 40 is equal to the blood pressure in appendage 42.

Detector waveform 106 is a stylized drawing displaying, in general, a waveform typical of the waveforms expected from the blood flow measurements of detector 52 or impedance plethysmograph 56. As described below, waveform 106 displays electrical "crossover signals" based upon the discontinuities detected by the invention when the blood flow starts or stops. During the time period from t1 to t2, the cuff pressure waveform 104 is less than the blood pressure waveform 102, therefore arterial blood is flowing, as indicated by the relatively high level of waveform 106. During the time period from t2 to t3, the cuff pressure waveform 104 is more than the blood pressure waveform 102, therefore arterial blood flow is prevented by cuff 40, as indicated by the relatively low level of waveform 106. At time t3, arterial blood flow is started, or allowed to flow by cuff 40, thus causing a discontinuity in waveform 106. At time t4, arterial blood flow is stopped from flowing by cuff 40, thus causing a discontinuity in waveform 106. Discontinuities occur in waveform 106 at each of the times t1 through t12. Such discontinuities are detected by electronic circuitry box 50 as indicating that the fluid pressure inside cuff 40 is equal to the arterial blood pressure inside appendage 42.

Waveform 108 is a representation of the Korotkoff noise signal blips picked up by microphone 54 at each of the times t1 through t12 when the pressure inside cuff 40 is equal to the arterial blood pressure inside appendage 42. Such blips are detected by electronic circuitry box 50.

Waveform 110 is identical to waveform 104 except that the small oscillometric variations occurring at each time t1 through t12 have been magnified. Waveform 112 is identical to waveform 102. Discontinuities are produced in the cuff pressure waveform 110 at each of the times t1 through t12 due to the fact that cuff 40 is part of a relatively closed fluidic system and thus its internal pressure is sensitive to changes in the volume of appendage 42. The expansion of arteries in appendage 42 when blood is allowed to start flowing causes the pressure in cuff 40 to increase slightly. The contraction of arteries in appendage 42 when blood is caused to stop flowing causes the pressure in cuff 40 to decrease slightly. The expansion and contraction of arteries cause volume changes in appendage 42 and result in the above mentioned discontinuities in waveform 110.

The slight increases and decreases in the pressure in cuff 40, as shown in waveform 112, produce the abovementioned discontinuities in waveform 110 which may be used by electronic circuitry box 50 in the same way as signals coming from detector 52. A high pass filter and amplifier of usual, conventional construction (not shown) may be used to condition the output of transducer 48 to provide a detection signal to replace the function of detector 52. Thus the need for a separate detector 52, microphone 54, or impedance plethysmograph 56 may be eliminated. Transducer 48 may be used both to measure the fluid pressure inside cuff 40, and to detect the times when the pressure inside cuff 40 is equal to the arterial blood pressure inside appendage 42.

What is claimed is:

1. A non-invasive blood pressure measurement system for performing blood pressure measurements on a real time basis comprising:
    a cuff composed of a flexible material for encircling a body appendage;
    pump means for supplying fluid to said cuff, said pump means including means for periodically varying the pressure of said fluid at a frequency higher than the rate at which the heart beats and over a sufficient pressure range that the periodically varying fluid pressure repeatedly passes through both the systolic and diastolic blood pressure levels during each heartbeat interval in said appendage during blood pressure measurement acquisition;
    means for detecting the times at which said fluid pressure is equal to said blood pressure;
    means for measuring said fluid pressure; and
    electrical circuit means for correlating said detecting means with said measuring means to thereby produce an electrical blood pressure signal indicative of the blood pressure in said appendage.

2. The blood pressure measurement system of claim 1 wherein said pump means comprises a pump piston slidably mounted to cyclically reciprocate in a pump cylinder; said pump cylinder having a port therein located at the lowermost position of the stroke of said pump piston, so that said pump cylinder is allowed to vent through said port when said pump piston reciprocates to the lowest point of its stroke during each cycle.

3. The blood pressure measurement system of claim 2 wherein said pump means further comprises a volume control means fluidicly connected to said cuff and said pump cylinder and having an externally adjustable fluid volume, so that the amplitude of the fluid pressure range generated by said pump may be externally adjusted, as by the operator of said measurement system.

4. The blood pressure measurement system of claim 3 wherein said volume control means comprises a volume control piston slidably mounted inside a volume control cylinder, and an adjustment screw threadably mounted through said volume control cylinder and connected to said volume control piston so that turning said screw moves said volume control piston along the length of said volume control cylinder.

5. The blood pressure measurement system of claim 1 wherein said measuring means comprises an electrical pressure transducer to measure the fluid pressure inside said cuff.

6. The blood pressure embodiment system of claim 5 wherein said detecting means comprises electrical circuitry connected to said electrical pressure transducer for detecting discontinuities in the fluid pressure waveform, and for producing an electrical crossover signal at each time that such a discontinuity occurs.

7. The blood pressure measurement system of claim 1 wherein said detector means comprises a microphone for mounting between said cuff and said appendage to thereby detect sounds emanating from said appendage.

8. The blood pressure measurement system of claim 1 wherein said detector means comprises a photoelectric blood pulsation sensor positioned adjacent said cuff.

9. The blood pressure measurement system of claim 1 in which said detector means is positioned a distance away from said cuff; and in which said electrical circuit means incorporates compensation means to correct for the time delay, caused by said distance, between said detector means and said measuring means.

10. The blood pressure measurement system of claim 1 in which said detector means comprises an impedance plethysmograph electrically connected to said appendage.

11. The blood pressure measurement system of claim 1 wherein said electrical circuit means comprises a gate allowing a signal from said measuring means to propagate as said electrical blood pressure signal only when said detector means indicates that said fluid pressure is equal to said blood pressure, thus producing an electrical blood pressure signal waveform having an envelope resembling the waveform of said blood pressure.

12. The blood pressure measurement system of claim 11 further comprising a waveform display means for presenting the envelope of the waveform of said electrical blood pressure signal.

13. The blood pressure measurement system of claim 1 wherein said electrical circuit means comprises a digital computer processor having inputs for said measuring means and said detector means, and having display means associated therewith for conveying information to the operator concerning the value of blood pressure in said appendage.

14. A method for measuring blood pressure comprising the steps of:
    applying an alternating external pressure to a body appendage, the period of said alternation being substantially shorter than the period of the blood pressure waveform in said appendage;
    detecting the times at which said external pressure is equal to said blood pressure;
    measuring said external pressure; and
    correlating said detected times with said measured pressure to thereby produce an electrical blood pressure signal indicative of the instantaneous value of blood pressure in said appendage.

15. The method of claim 14 wherein said step of correlating consists of the steps of:
    inputting the results of said step of measuring to a gate circuit;
    gating said gate circuit with the results of said step of detecting to thereby produce said electrical blood pressure signal.

16. The method of claim 14 or claim 15 further including the step of displaying said electrical blood pressure signal so that a waveform is shown consisting of a sequence of spaced-apart spikes, the height of each of said spikes indicating an instantaneous blood pressure value, and wherein a new one of said spikes related to said blood pressure signal is displayed when said external pressure is equal to said blood pressure.

17. The method of claim 14 wherein said step of correlating consists of the steps of:
sampling the results of said step of detecting;
sampling the results of said step of measuring;
processing the results of the two previous sampling steps in a digital computer to correlate said detected times with said measured pressures to thereby produce said electrical blood pressure signal.

* * * * *

UNITED STATES PATENT AND TRADEMARK OFFICE
CERTIFICATE OF CORRECTION

PATENT NO. : 4,343,314
DATED : August 10, 1982
INVENTOR(S) : Bohumir Sramek

It is certified that error appears in the above-identified patent and that said Letters Patent are hereby corrected as shown below:

Column 6, Line 18, delete "140" and substitute --104--.

Column 6, Line 51, delete "$t_4$" and substitute --$t_3$--.

Column 8, Line 7, delete "embodiment" and substitute --measurement--.

Signed and Sealed this

Thirty-first Day of January 1984

[SEAL]

Attest:

Attesting Officer

GERALD J. MOSSINGHOFF

Commissioner of Patents and Trademarks